US010619175B2

United States Patent
Rabe et al.

(10) Patent No.: US 10,619,175 B2
(45) Date of Patent: Apr. 14, 2020

(54) PROCESS FOR PRODUCING A PUFA-CONTAINING FEEDSTUFF BY EXTRUDING A PUFA-CONTAINING BIOMASS

(71) Applicant: Evonik Degussa GmbH, Essen (DE)

(72) Inventors: Christian Rabe, Grossostheim (DE); Amelia Claudia Silva, Hanau (DE); Stefan Eils, Gründau (DE); Horst Priefert, Ostbevern (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 15/516,044

(22) PCT Filed: Sep. 22, 2015

(86) PCT No.: PCT/EP2015/071707
§ 371 (c)(1),
(2) Date: Mar. 31, 2017

(87) PCT Pub. No.: WO2016/050559
PCT Pub. Date: Apr. 7, 2016

(65) Prior Publication Data
US 2017/0306365 A1   Oct. 26, 2017

(30) Foreign Application Priority Data

Oct. 2, 2014   (EP) .................................... 14187479

(51) Int. Cl.
| | | |
|---|---|---|
| *C12P 7/64* | (2006.01) |
| *A23K 10/16* | (2016.01) |
| *A23K 20/158* | (2016.01) |
| *A23K 50/80* | (2016.01) |
| *A23K 40/25* | (2016.01) |
| *A23K 20/163* | (2016.01) |
| *A23K 40/30* | (2016.01) |
| *A23K 10/12* | (2016.01) |
| *A21D 2/16* | (2006.01) |
| *A23D 7/00* | (2006.01) |

(Continued)

(52) U.S. Cl.
CPC ............ *C12P 7/6472* (2013.01); *A21D 2/165* (2013.01); *A23D 7/001* (2013.01); *A23D 7/005* (2013.01); *A23D 7/0053* (2013.01); *A23D 7/0056* (2013.01); *A23K 10/12* (2016.05); *A23K 10/16* (2016.05); *A23K 20/158* (2016.05); *A23K 20/163* (2016.05); *A23K 40/25* (2016.05); *A23K 40/30* (2016.05); *A23K 50/80* (2016.05); *A61K 31/20* (2013.01); *C11B 1/025* (2013.01); *C11B 1/10* (2013.01); *A23D 9/00* (2013.01); *C11B 5/00* (2013.01); *Y02A 40/818* (2018.01)

(58) Field of Classification Search
CPC .... A23K 20/158; A23K 10/12; A23K 20/163; A23K 40/25; A23K 50/80; A23K 10/16; A23K 40/30; A23K 40/10; A23K 40/20; A23K 50/40; A23K 1/007; A23K 1/008; A23K 1/164; A23K 1/188; A23K 20/28; A23K 3/005; C12P 7/6472; C12P 19/04; C12P 7/6427; C12P 23/00; C12P 7/66; C12P 21/02; C12P 7/6409; A21D 2/165; A21D 2/16; A23D 7/001; A23D 7/005; A23D 7/0053; A23D 7/0056; A23D 9/00; A61K 31/20; A61K 31/202; A61K 35/66; A61K 39/145; A61K 8/30; A61K 8/37; A61K 8/92; A61K 8/97; A61K 8/99; A61K 2039/5258; C11B 1/025; C11B 1/10; C11B 5/00; C11B 1/104; C11B 1/06; C11B 3/12; C11B 3/16; C12N 15/8247; C12N 9/1029; C12N 15/52; C12N 1/10; C12N 1/12; C12N 1/00; C12N 2760/16123; C12N 2760/16134; C12N 2760/16152; C12N 7/00; C12N 9/2402; C12N 1/005; C12N 1/20; C11C 3/003; C11C 1/08; C07C 69/533; C07C 67/03; C07C 67/08; C07C 51/42; C07C 53/126; C07C 67/60; C07C 69/587; Y02A 40/818; A23L 29/065; A23L 31/00; A23L 33/12; C07F 9/103; A23V 2002/00; C07K 14/005; C12Y 302/01018; A23P 10/22; Y10S 435/911
See application file for complete search history.

(56) References Cited

U.S. PATENT DOCUMENTS

| | | |
|---|---|---|
| 2,123,134 A | 7/1938 | Cowgill |
| 2,177,031 A | 10/1939 | Tanner |

(Continued)

FOREIGN PATENT DOCUMENTS

| | | |
|---|---|---|
| AU | 771 809 B2 | 6/2001 |
| CH | 646 729 | 12/1984 |

(Continued)

OTHER PUBLICATIONS

Jain et al, "Extracell. Polysaccharide Prod. by Thraustochytrid Protists" Marine Biotech., pp. 184-192, 2005.*

(Continued)

*Primary Examiner* — Deborah K Ware
(74) *Attorney, Agent, or Firm* — Law Office of: Michael A. Sanzo, LLC

(57) ABSTRACT

In accordance with the invention, it was found, surprisingly, that a polyunsaturated fatty acids (PUFAs)-comprising biomass with other feedstuff components can be extruded at a low energy input of 12-28 Wh/kg to give an extrudate with a very high oil load capacity.

18 Claims, No Drawings

(51) Int. Cl.
  *A23D 7/005* (2006.01)
  *A61K 31/20* (2006.01)
  *C11B 1/02* (2006.01)
  *C11B 1/10* (2006.01)
  *A23D 9/00* (2006.01)
  *C11B 5/00* (2006.01)

(56) References Cited

U.S. PATENT DOCUMENTS

| | | |
|---|---|---|
| 2,513,369 A | 7/1950 | Shaw |
| 3,257,737 A | 6/1966 | Thomas |
| 3,257,738 A | 6/1966 | Margittai et al. |
| 3,437,489 A | 4/1969 | Seiji et al. |
| 3,773,527 A | 11/1973 | Ruggerone |
| 3,920,815 A | 11/1975 | Harvey et al. |
| 4,160,040 A | 7/1979 | Luca et al. |
| 4,209,538 A | 6/1980 | Woodruff |
| 4,228,197 A | 10/1980 | Means |
| 4,335,150 A | 6/1982 | Hosaka et al. |
| 4,592,762 A | 6/1986 | Babu et al. |
| 4,683,139 A | 7/1987 | Cheng |
| 5,113,597 A | 5/1992 | Sylla |
| 5,130,242 A | 7/1992 | Barclay |
| 5,298,271 A | 3/1994 | Takashina et al. |
| 5,340,594 A | 8/1994 | Barclay |
| 5,340,742 A | 8/1994 | Barclay |
| 5,434,183 A | 7/1995 | Larsson-Backstrom |
| 5,518,918 A | 5/1996 | Barclay |
| 5,567,732 A | 10/1996 | Kyle et al. |
| 5,574,065 A | 11/1996 | Trimbo |
| 5,622,710 A | 4/1997 | Binder et al. |
| 5,656,319 A | 8/1997 | Barclay |
| 5,698,244 A | 12/1997 | Barclay |
| 5,700,506 A | 12/1997 | Mudahar |
| 5,700,837 A | 12/1997 | Trimbo |
| 5,840,358 A | 11/1998 | Hofler et al. |
| 6,068,874 A | 5/2000 | Grocholski |
| 6,117,905 A | 9/2000 | Higashiyama et al. |
| 6,158,147 A | 12/2000 | Smith et al. |
| 6,166,230 A | 12/2000 | Bijl et al. |
| 6,248,909 B1 | 6/2001 | Akimoto et al. |
| 6,255,505 B1 | 7/2001 | Bijl et al. |
| 6,326,037 B1 | 12/2001 | Mann et al. |
| 6,372,460 B1 | 4/2002 | Gladue et al. |
| 6,410,281 B1 | 6/2002 | Barclay |
| 6,441,208 B2 | 8/2002 | Bijl et al. |
| 6,451,567 B1 | 9/2002 | Barclay |
| 6,602,690 B2 | 8/2003 | Kawashima et al. |
| 6,607,900 B2 | 8/2003 | Bailey et al. |
| 6,727,373 B2 | 4/2004 | Bijl et al. |
| 6,812,009 B2 | 11/2004 | Gladue et al. |
| 6,977,167 B2 | 12/2005 | Barclay |
| 7,067,145 B2 | 6/2006 | Place et al. |
| 7,259,006 B2 | 8/2007 | Komazawa et al. |
| 7,381,558 B2 | 6/2008 | Barclay |
| 7,470,527 B2 * | 12/2008 | Streekstra ............... A23D 9/00 426/601 |
| 7,514,096 B2 | 4/2009 | Haraldsson et al. |
| 7,514,244 B2 | 4/2009 | Tanaka et al. |
| 7,579,174 B2 | 8/2009 | Bailey et al. |
| 7,709,236 B2 | 5/2010 | Akimoto et al. |
| 7,723,386 B2 | 5/2010 | Akimoto et al. |
| 7,732,170 B2 | 6/2010 | Bailey et al. |
| 7,847,113 B2 | 12/2010 | Kawashima et al. |
| 7,863,026 B2 | 1/2011 | Komazawa et al. |
| 7,910,604 B2 | 3/2011 | Vasquez-Anon et al. |
| 7,935,365 B2 | 5/2011 | Dror et al. |
| 8,030,348 B2 | 10/2011 | Sampalis |
| 8,052,992 B2 | 11/2011 | Dror et al. |
| 8,124,384 B2 | 2/2012 | Bailey et al. |
| 8,124,385 B2 | 2/2012 | Bailey et al. |
| 8,129,172 B2 | 3/2012 | Barclay |
| 8,143,310 B2 | 3/2012 | Wang |
| 8,163,515 B2 | 4/2012 | Burja et al. |
| 8,187,846 B2 | 5/2012 | Bailey et al. |
| 8,207,363 B2 | 6/2012 | Apt et al. |
| 8,216,812 B2 | 7/2012 | Bailey et al. |
| 8,217,151 B2 | 7/2012 | Schaap et al. |
| 8,236,854 B2 | 8/2012 | Akimoto et al. |
| 8,241,868 B2 | 8/2012 | Higashiyama et al. |
| 8,278,351 B2 | 10/2012 | Sampalis |
| 8,288,133 B2 | 10/2012 | Bailey et al. |
| 8,288,134 B2 | 10/2012 | Bailey et al. |
| 8,334,363 B2 | 12/2012 | Hurd et al. |
| 8,343,753 B2 | 1/2013 | Chilton et al. |
| 8,367,774 B2 | 2/2013 | Frank |
| 8,420,349 B2 | 4/2013 | Kralovec et al. |
| 8,900,831 B2 | 12/2014 | Rusing et al. |
| 8,945,886 B2 | 2/2015 | Katano et al. |
| 8,999,663 B2 * | 4/2015 | Avgousti ............... A23K 40/20 435/41 |
| 9,045,785 B2 * | 6/2015 | Pfeifer, III ............ C12P 7/6427 |
| 9,072,311 B2 | 7/2015 | Harel et al. |
| 9,101,151 B2 | 8/2015 | Kobzeff et al. |
| 9,414,612 B2 | 8/2016 | Apt et al. |
| 9,493,798 B2 | 11/2016 | Higashiyama et al. |
| 9,649,609 B2 | 5/2017 | Alt et al. |
| 9,848,623 B2 | 12/2017 | Bailey et al. |
| 2002/0110582 A1 | 8/2002 | Place et al. |
| 2003/0143659 A1 | 7/2003 | Bijl et al. |
| 2005/0118208 A1 | 6/2005 | Bewert |
| 2005/0129739 A1 | 6/2005 | Kohn et al. |
| 2005/0202148 A1 * | 9/2005 | Streekstra ............... A23D 9/00 426/601 |
| 2005/0287263 A1 | 12/2005 | Mayer |
| 2006/0051484 A1 | 3/2006 | Yamaguchi et al. |
| 2006/0068019 A1 | 3/2006 | Daiziel |
| 2006/0094089 A1 | 5/2006 | Barclay |
| 2006/0160203 A1 | 7/2006 | Barclay |
| 2006/0188969 A1 | 8/2006 | Barclay |
| 2006/0265766 A1 | 11/2006 | Kyle et al. |
| 2006/0286205 A1 | 12/2006 | Fichtali et al. |
| 2007/0032383 A1 | 2/2007 | Newell |
| 2007/0082008 A1 | 4/2007 | Harel et al. |
| 2007/0092955 A1 | 4/2007 | De Laat et al. |
| 2007/0243307 A1 | 10/2007 | Abril et al. |
| 2007/0244192 A1 | 10/2007 | Metz |
| 2007/0248738 A1 | 10/2007 | Abril et al. |
| 2007/0248739 A1 | 10/2007 | Abril et al. |
| 2008/0026128 A1 | 1/2008 | Yamaguchi et al. |
| 2008/0032381 A1 | 2/2008 | Bailey et al. |
| 2008/0038800 A1 | 2/2008 | Ruecker et al. |
| 2008/0096964 A1 | 4/2008 | Subramanian et al. |
| 2008/0166780 A1 | 7/2008 | Barclay |
| 2008/0199923 A1 | 8/2008 | Barclay |
| 2008/0254177 A1 | 10/2008 | Lin et al. |
| 2009/0053342 A1 * | 2/2009 | Streekstra ............... A23D 9/00 424/780 |
| 2009/0064567 A1 | 3/2009 | Lippmeier et al. |
| 2009/0136637 A1 | 5/2009 | Janssen et al. |
| 2009/0162892 A1 | 6/2009 | Pompejus et al. |
| 2009/0182050 A1 | 7/2009 | Barrow et al. |
| 2009/0202672 A1 | 8/2009 | Hartnell |
| 2009/0263889 A1 | 10/2009 | Wumpelmann |
| 2009/0274817 A1 | 11/2009 | Yamaguchi et al. |
| 2009/0285969 A1 | 11/2009 | Schaap et al. |
| 2010/0010088 A1 | 1/2010 | Chilton et al. |
| 2010/0086638 A1 | 4/2010 | Kyle et al. |
| 2010/0151112 A1 | 6/2010 | Franklin et al. |
| 2010/0159583 A1 | 6/2010 | Onose |
| 2010/0239712 A1 | 9/2010 | Brooks et al. |
| 2010/0266681 A1 | 10/2010 | Holmeide |
| 2010/0285105 A1 | 11/2010 | Radianingtyas |
| 2010/0297292 A1 | 11/2010 | Brooks et al. |
| 2010/0297295 A1 | 11/2010 | Brooks et al. |
| 2010/0297323 A1 | 11/2010 | Brooks et al. |
| 2010/0297331 A1 | 11/2010 | Brooks et al. |
| 2010/0303961 A1 | 12/2010 | Brooks et al. |
| 2010/0303989 A1 | 12/2010 | Brooks et al. |
| 2010/0303990 A1 | 12/2010 | Brooks et al. |
| 2011/0054029 A1 | 3/2011 | Kuhrts |
| 2011/0086128 A1 | 4/2011 | Abril et al. |
| 2011/0117068 A1 | 5/2011 | Lang et al. |
| 2011/0129884 A1 | 6/2011 | Luy |

(56) References Cited

U.S. PATENT DOCUMENTS

| | | | |
|---|---|---|---|
| 2011/0166228 A1 | 7/2011 | Holmeide et al. | |
| 2011/0177031 A1 | 7/2011 | Apt et al. | |
| 2011/0189228 A1* | 8/2011 | Bayne | C12N 1/12 424/204.1 |
| 2011/0195448 A1* | 8/2011 | Lippmeier | C12N 1/22 435/41 |
| 2011/0195449 A1* | 8/2011 | Lippmeier | C12N 1/12 435/41 |
| 2011/0203168 A1 | 8/2011 | Franklin et al. | |
| 2011/0258915 A1 | 10/2011 | Subhadra | |
| 2011/0287158 A1 | 11/2011 | Yamaguchi et al. | |
| 2012/0213905 A1 | 8/2012 | Nichols | |
| 2012/0237578 A1 | 9/2012 | Lei et al. | |
| 2013/0045226 A1 | 2/2013 | Avgousti et al. | |
| 2013/0046020 A1* | 2/2013 | Liang | C07C 57/03 514/560 |
| 2013/0046105 A1* | 2/2013 | Avgousti | A23K 40/20 554/165 |
| 2013/0172590 A1* | 7/2013 | Pfeifer, III | C12P 7/6427 554/224 |
| 2013/0302470 A1 | 11/2013 | Becker et al. | |
| 2014/0017742 A1* | 1/2014 | Streekstra | A23D 9/00 435/134 |
| 2015/0044356 A1* | 2/2015 | Bootsma | A23K 10/12 426/656 |
| 2015/0223492 A1* | 8/2015 | Pfeifer, III | C12P 7/6427 554/224 |
| 2016/0183565 A1 | 6/2016 | Rudinger et al. | |
| 2016/0227816 A1 | 8/2016 | Alt et al. | |
| 2016/0249642 A1 | 9/2016 | Rabe et al. | |
| 2016/0255862 A1 | 9/2016 | Oelmann et al. | |
| 2017/0121742 A1 | 5/2017 | Aijawi et al. | |
| 2017/0245523 A1* | 8/2017 | Pfeifer, III | C12P 7/6427 |
| 2017/0290356 A1 | 10/2017 | Silva et al. | |
| 2017/0295823 A1 | 10/2017 | Rabe et al. | |
| 2017/0295824 A1 | 10/2017 | Priefert et al. | |
| 2017/0298318 A1 | 10/2017 | Rabe et al. | |
| 2017/0303561 A1 | 10/2017 | Durhuus et al. | |

FOREIGN PATENT DOCUMENTS

| | | |
|---|---|---|
| CN | 101 999 552 | 4/2011 |
| CN | 102 687 810 | 9/2012 |
| CN | 103 070 293 | 5/2013 |
| CN | 103 385 390 | 11/2013 |
| DE | 10 2006 026 328 | 1/2008 |
| GB | 1 397 410 | 6/1975 |
| GB | 1 560 478 | 10/1976 |
| GB | 2 324 701 | 11/1998 |
| GB | 2 437 909 | 11/2007 |
| WO | WO 91/07498 | 5/1991 |
| WO | WO 94/08467 | 4/1994 |
| WO | WO 97/36996 | 10/1997 |
| WO | WO 97/37032 | 10/1997 |
| WO | WO 98/49904 | 11/1998 |
| WO | WO 01/54510 | 8/2001 |
| WO | WO 02/00035 | 1/2002 |
| WO | WO 2006/085672 | 8/2006 |
| WO | WO 2006/124598 | 11/2006 |
| WO | WO 2006/136539 | 12/2006 |
| WO | WO 2007/074479 | 7/2007 |
| WO | WO 2008/019887 | 2/2008 |
| WO | WO 2008/049512 | 5/2008 |
| WO | WO 2010/090979 | 8/2010 |
| WO | WO 2010/120923 | 10/2010 |
| WO | WO 2010/128312 | 11/2010 |
| WO | WO 2011/006261 | 1/2011 |
| WO | WO 2013/022485 | 2/2013 |
| WO | WO 2014/045191 | 3/2014 |
| WO | WO 2014/122087 | 8/2014 |
| WO | WO 2014/122092 | 8/2014 |

OTHER PUBLICATIONS

Suomalainen, et al., "The Fatty Acid Composition of Baker's and Brewer's Yeast," *Chem. Phys. Lipids* 2:296-315 (1968).
Technicial Information 1251 (2017) http://www.sipernat.com/sites/lists/RE/DocumentsSI/TI-1251-AEROSIL-and-SIPERNAT-Silica-Versatile-Raw-Materials-for-Personal-Care-Formulations-EN.pdf download Apr. 11, 2018 (Year: 2017).
Chen, et al., "Whole cell algae powder used for increasing docosahexanoic acid content in milk of high-yielding mammal, comprises docohexanoic acid containing algae cell slurry, emulsifier, antioxidant, filler, packaging material, dispersant and water," WPI/THOMPSON, Bd. 2011, Nr. 44, (Apr. 6, 2011); XP-002721747.
Uemura, "Synthesis and production of unsaturated and polyunsaturated fatty acids in yeast: current state and perspectives," *Appl. Microbiol. Biotechnol.* 95:1-12 (May 2012).
Visentainer, et al., "Influence of diets enriched with flaxseed oil on the α-linolenic, eicosapentaenoic and docosahexaenoic fatty acid in Nile tilapia (*Oreochromis niloticus*)," *Food Chemistry* 90:557-560 (May 2005).
Restriction Requirement from copending U.S. Appl. No. 15/516,058 dated Oct. 12, 2018.
Response to Restriction Requirement from copending U.S. Appl. No. 15/516,058, filed Dec. 12, 2018.
Amendment to accompany Response to Restriction Requirement from copending U.S. Appl. No. 15/516,058, filed Dec. 12, 2018.
Hammond, et al., "Safety Assessment of DHA-Rich Microalgae from *Schizochytrium* sp.," *Regulatory Toxicology and Pharmacology* 33(2):192-204 (Apr. 2001).
Chang, K.J.L., "New Australian thraustochytrids: A Renewable Source of Biofuels, Omega-3 Oils and other Bioproducts," Thesis; University of Tasmania; (Aug. 2013).
Restriction Requirement for copending U.S. Appl. No. 15/516,024, dated Mar. 4, 2019.
Non Final Office Action for copending U.S. Appl. No. 15/516,058, dated Mar. 12, 2019.
Response to Restriction Requirement filed May 4, 2019, for copending U.S. Appl. No. 15/516,024.
Restriction Requirement for copending U.S. Appl. No. 15/516,023, dated May 7, 2019.
Amendment and Response to Non Final Office Action filed Jun. 22, 2019, for copending U.S. Appl. No. 15/515,058.
Restriction Requirement for copending U.S. Appl. No. 15/516,022, dated Jun. 26, 2019.
Response to Restriction Requirement filed Jul. 5, 2019, for copending U.S. Appl. No. 15/516,023.
Keleb, et al., "Continous twin screw extrusion for the wet granulation of lactose," *International Journal of Pharmaceutics* 239:69-80 (2002).
English language translation International Search Report for PCT/EP2015/071707 filed Sep. 22, 2015.
English language translation of the Written Opinion of the International Searching Authority for PCT/EP2015/071707 filed Sep. 22, 2015.
English language translation of the International Preliminary Report on Patentability for PCT/EP2015/071707 filed Sep. 22, 2015.
European Search Report for EP 14 18 7479 filed Oct. 2, 2014.
English translation of the International Search Report for PCT/EP2015/071666 filed Sep. 22, 2015 for copending U.S. Appl. No. 15/516,022.
English language translation of the Written Opinion of the International Searching Authority for PCT/EP2015/071666 filed Sep. 22, 2015 for copending U.S. Appl. No. 15/516,022.
English language translation of the International Preliminary Report on Patentability for PCT/EP2015/071666 filed Sep. 22, 2015 for copending U.S. Appl. No. 15/516,022.
European Search Report with partial machine translation for EP 14 18 7485 filed Oct. 2, 2014 for copending U.S. Appl. No. 15/516,022.
English translation of the International Search Report for PCT/EP2015/071635 filed Sep. 22, 2015 for copending U.S. Appl. No. 15/516,024.
English language translation of the Written Opinion of the International Searching Authority for PCT/EP2015/071635 filed Sep. 22, 2015 for copending U.S. Appl. No. 15/516,024.

(56) References Cited

OTHER PUBLICATIONS

English language translation of the International Preliminary Report on Patentability for PCT/EP2015/071635 filed Sep. 22, 2015 for copending U.S. Appl. No. 15/516,024.
European Search Report with partial machine translation for EP 14 18 7471 filed Oct. 2, 2014 for copending U.S. Appl. No. 15/516,024.
English translation of the International Search Report for PCT/EP2015/071689 filed Sep. 22, 2015 for copending U.S. Appl. No. 15/516,023.
English language translation of the Written Opinion of the International Searching Authority for PCT/EP2015/071689 filed Sep. 22, 2015 for copending U.S. Appl. No. 15/516,023.
English language translation of the International Preliminary Report on Patentability for PCT/EP2015/071689 filed Sep. 22, 2015 for copending U.S. Appl. No. 15/516,023.
European Search Report with partial machine translation for EP 14 18 7467 filed Oct. 2, 2014 for copending U.S. Appl. No. 15/516,023.
English translation of the International Search Report for PCT/EP2015/072824 filed Oct. 2, 2015 for copending U.S. Appl. No. 15/516,058.
English language translation of the Written Opinion of the International Searching Authority for PCT/EP2015/072824 filed Oct. 2, 2015 for copending U.S. Appl. No. 15/516,058.
English language translation of the International Preliminary Report on Patentability for PCT/EP2015/072824 filed Oct. 2, 2015 for copending U.S. Appl. No. 15/516,058.
European Search Report with partial machine translation for EP 14 18 7471 filed Oct. 2, 2014 for copending U.S. Appl. No. 15/516,058.
Asha, et al., "Effect of sea weed, sea grass and powdered algae in rearing the hatchery produced juveniles of *Holothuria* (metriatyla) *scabra*, jeager," *Proceedings of the National Symposium on Recent Trends in Fisheries*, (2004).
Baeverfjord, et al., "Low feed pellet water stability and fluctuating water salinity cause separation and accumulation of dietary oil in the stomach of rainbow trout (*Oncorhrynchus mykiss*)," *Aquaculture* 261(4):1335-1345 (Dec. 2006).
Carter, et al., "Potential of Thraustochytrids to Partially Replace Fish Oil in Atlantic Salmon Feeds," *Marine Biotechnology* 5:480-492 (Oct. 2002).
Hondo, et al.,"*Schizochytrium limacinum* sp. nov., a new thraustochytrid from a mangrove area in the west Pacific Ocean," *Mycological Research* 102(4):439-448 (Apr. 1998).
Jain, et al., "Extracellular Polysaccharide Production by Thraustochytrid Protists," *Marine Biotechnology* 7:184-192 (published online May 2005).
Miller, et al., Replacement of fish oil with thraustochytrid *Schizochytrium* sp. L oil in Atlantic salmon parr (*Salmo salar* L) diets, *Comparative Biochemistry and Physiology, Part A* 148:382-392 (available online May 2007).
Nakahara, et al., "Production of Docosahexaenoic and Docosapentaenioc Acids by *Schizochytrium* sp. Isolated from Yap Islands," *Journal of American Oil Chemists' Society* 73(11): 1421-1425 (Nov. 1996).
Prabu, et al., "Effect of sodium sulphate salinity for production of docosahexaenoic acid (DHA) by *Thraustochytrids aureum* RAK-21," *Asian Biomedicine* 6(5):693-701 (Oct. 2012).
Taxonomy Browser: *Aurantiochytrium limacinum*; taxonomy ID: 87102 (Jan. 2015).
XP-002721747; Database WPI Thomson Scientific, London GB; (Sep. 2013).
XP-002534705; Degussa: "Product Information SIPERNAT D17," Internet citation (Sep. 2004).
U.S. Appl. No. 14/904,665, filed Jan. 12, 2016, US-2016/0183565, Jun. 30, 2016, Rudinger.
U.S. Appl. No. 15/027,429, filed Apr. 5, 2016, US-2016/0249642, Sep. 1, 2016, Rabe.
U.S. Appl. No. 15/516,038, filed Mar. 31, 2017, Rabe.
U.S. Appl. No. 15/516,023, filed Mar. 31, 2017, Silva.
U.S. Appl. No. 15/516,024, filed Mar. 31, 2017, Priefert.
U.S. Appl. No. 15/516,022, filed Mar. 31, 2017, Rabe.
U.S. Appl. No. 15/516,058, filed Mar. 31, 2017, Durhuus.
Office Action dated Sep. 17, 2019, for copending U.S. Appl. No. 15/516,022.
Amendment and Response to Office Action filed Nov. 24, 2019, for copending U.S. Appl. No. 15/516,023.
Amendment and Response to Office Action filed Dec. 16, 2019, for copending U.S. Appl. No. 15/516,024.

* cited by examiner

PROCESS FOR PRODUCING A PUFA-CONTAINING FEEDSTUFF BY EXTRUDING A PUFA-CONTAINING BIOMASS

CROSS REFERENCE TO RELATED APPLICATIONS

The present application is US national stage of international application PCT/EP2015/071707, which had an international filing date of Sep. 22, 2015, and which was published in German under PCT Article 21(2) on Apr. 7, 2016. Priority is claimed to European application EP 14187479.2, filed on Oct. 2, 2014.

The present invention relates to a process for the preparation of a polyunsaturated fatty acids (PUFAs)-comprising feedstuff by extruding a PUFAs-comprising biomass.

Processes for the preparation of PUFAs (polyunsaturated fatty acids)-comprising biomass have already been described in the art. Processing a suitable biomass together with other feedstuff constituents may be effected for example by extrusion. Here, the PUFAs-comprising biomass is used as an alternative source for PUFAs since fish oil, which has traditionally been used as a source for PUFAs, is no longer available in a sufficient quantity due to overfishing.

It was an object of the present invention to provide a feedstuff which comprises PUFAs, in particular omega-3 fatty acids, and which has the highest possible oil load capacity. This is because feedstuffs which are coated with oil at a later point in time have proved to be especially suitable feedstuffs, especially in aquaculture.

Previously, it has been found that, when using fish oil for the preparation of the feedstuff, the energy input required for carrying out the extrusion is very high if a product with a desired oil load capacity is to be obtained. When using fish oil as the source for omega-3 fatty acids, the remaining feedstuff components are extruded first, and the resulting extrudate is subsequently loaded with fish oil and, optionally, further oil components.

Surprisingly, it has now been found in accordance with the invention that, when using a biomass which comprises PUFAs, in particular omega-3 fatty acids, a very much lower energy input suffices to obtain an extrudate with the desired oil load capacity. In this context, an energy input of not more than 28 Wh/kg has proved to be sufficient for obtaining the desired product properties, with an energy input of 12-28 Wh/kg being advantageous.

An especially low energy input of not more than 22 Wh/kg, in particular 18-22 Wh/kg, suffices in particular when the biomass used for preparing the feedstuff is a PUFAs-comprising biomass which has been obtained by being grown at a sulphate concentration such that the sulphate content of the resulting biomass is 25 to 60 g/kg, in particular 25 to 50, 25 to 40 or 25 to 35 g/kg, based on the dry matter.

A first subject matter of the present invention is therefore a process for the preparation of a PUFAs-comprising feedstuff, characterized in that a PUFAs-comprising biomass is extruded together with further feedstuff components at an energy input of 12-28 Wh/kg. In this context, the extrusion preferably takes place at an energy input of 14-26, in particular 16-24, especially preferably 18-22 Wh/g.

A screw or twin-screw extruder is preferably employed in the extrusion process. The extrusion process is preferably carried out at a temperature of 80-220° C., particularly 80-130° C., a pressure of 10-40 Bar, and a shaft rotational speed of 100-1000 rpm, particularly 300-700 rpm. The residence time of the mixture introduced is preferably 5-30 seconds, in particular 10-20 seconds.

The extrudate generated preferably has a diameter of from 1 to 14 mm, preferably 2 to 12 mm, in particular 2 to 6 mm, and preferably also has a length of from 1 to 14 mm, preferably 2 to 12 mm, in particular 2 to 6 mm. The length of the extrudate is set by employing a cutting tool during the extrusion. The length of the extrudate is preferably chosen such that it approximately corresponds to the diameter of the extrudate. The diameter of the extrudate is set by the selection of the die diameter.

The oil load capacity is directly connected with the expansion of the extrudate during the extrusion process. The greater the expansion during extrusion, the higher the oil load capacity of the extrudate obtained.

The oil load capacity of an extrudate according to the invention amounts to preferably at least 0.25 g of oil per g of extrudate, especially preferably to at least 0.3 g of oil per g of extrudate, in particular at least 0.35 g of oil per g of extrudate.

A further subject matter of the present invention is therefore also a PUFAs-comprising feedstuff, in particular feedstuff extrudate, which has an oil load capacity of at least 0.25 g of oil per g of extrudate, in particular at least 0.275 or 0.30 g of oil per g of extrudate, preferably at least 0.325 or 0.35 g of oil per g of extrudate.

By exhausting the oil load capacity, extrudates with a total fat content of at least 25% by weight or at least 27.5% by weight, in particular at least 30% by weight or at least 32.5% by weight, especially also those with a total fat content of over 35% by weight, can be realised in this manner.

The extrudate according to the invention preferably has a bulk density of 400-500 g/l.

The extrusion process may optionally comprise a compaction step and/or a compression step.

It is preferred to intimately mix the components with each other before carrying out the extrusion process. This is preferably carried out in a drum equipped with vanes. In this mixing step, a preferred embodiment includes an injection of steam, in particular so as to bring about the swelling of the starch which is preferably present. In this case, the injection of steam is preferably carried out under a pressure of 1 to 5 bar, especially preferably under a pressure of 2 to 4 bar.

Before being mixed with the algal biomass, the further foodstuff or feedstuff ingredients are preferably comminuted—if required—so as to ensure that a homogeneous mixture is obtained in the mixing step. The comminuting of the further foodstuff or feedstuff ingredients may be carried out, for example, using a hammer mill.

In an embodiment which is preferred in accordance with the invention, the extrusion process is followed by loading the resulting extrudate with oil. To this end, the extrudate is preferably first dried to a moisture content of not more than 5% by weight. Loading of the extrudate with oil may in accordance with the invention take place for example by placing the extrudate into oil or spraying the extrudate with oil; however, in accordance with the invention, it preferably takes place by vacuum coating.

The preparation of PUFAs-comprising biomasses which can be employed in accordance with the invention is described extensively in the prior art. The cells used may, in this context, in particular be cells which already naturally produce PUFAs (polyunsaturated fatty acids), however, they may also be cells which, as the result of suitable genetic engineering methods, have been made capable of producing PUFAs. In this context, the production may be autotrophic, mixotrophic or heterotrophic.

The biomass preferably comprises cells which produce PUFAs heterotrophically. The cells according to the invention preferably take the form of algae, fungi, particularly yeasts, or protists. The cells are especially preferably of microbial algae or fungi.

Suitable cells of oil-producing yeasts are, in particular, strains of *Yarrowia, Candida, Rhodotorula, Rhodosporidium, Cryptococcus, Trichosporon* and *Lipomyces*.

The biomass according to the invention preferably comprises cells, and preferably consists essentially of such cells, of the taxon Labyrinthulomycetes (Labyrinthulea, net slime fungi, slime nets), in particular those from the family of Thraustochytriaceae. The family of the Thraustochytriaceae includes the genera *Althomia, Aplanochytrium, Elnia, Japonochytrium, Schizochytrium, Thraustochytrium, Aurantiochytrium, Oblongichytrium* and *Ulkenia*. The biomass particularly preferably comprises cells from the genera *Thraustochytrium, Schizochytrium, Aurantiochytrium* or *Oblongichytrium*, above all those from the genus *Aurantiochytrium*.

Within the genus *Aurantiochytrium*, the species *Aurantiochytrium limacinum* (previously also referred to as *Schizochytrium limacinum*) is preferred in accordance with the invention. The strain *Aurantiochytrium limacinum* SR21 is very especially preferably employed in accordance with the invention.

In accordance with the invention, the polyunsaturated fatty acid (PUFA) is preferably a highly-unsaturated fatty acid (HUFA).

The cells present in the biomass are preferably distinguished by the fact that they contain at least 20% by weight, preferably at least 30% by weight, in particular at least 35% by weight, of PUFAs, in each case based on cell dry matter.

In a preferred embodiment, the majority of the lipids in this case is present in the form of triglycerides, with preferably at least 50% by weight, in particular at least 75% by weight and, in an especially preferred embodiment, at least 90% by weight of the lipids present in the cell being present in the form of triglycerides.

According to the invention, polyunsaturated fatty acids (PUFAs) are understood to mean fatty acids having at least two, particularly at least three, C—C double bonds. According to the invention, highly-unsaturated fatty acids (HUFAs) are preferred among the PUFAs. According to the invention, HUFAs are understood to mean fatty acids having at least four C—C double bonds.

The PUFAs may be present in the cell in free form or in bound form. Examples of the presence in bound form are phospholipids and esters of the PUFAs, in particular monoacyl-, diacyl- and triacylglycerides. In a preferred embodiment, the majority of the PUFAs is present in the form of triglycerides, with preferably at least 50% by weight, in particular at least 75% by weight and, in an especially preferred embodiment, at least 90% by weight of the PUFAs present in the cell being present in the form of triglycerides.

Preferred PUFAs are omega-3 fatty acids and omega-6 fatty acids, with omega-3 fatty acids being especially preferred. Preferred omega-3 fatty acids here are the eicosapentaenoic acid (EPA, 20:5ω-3), particularly the (5Z,8Z,11Z,14Z,17Z)-eicosa-5,8,11,14,17-pentaenoic acid, and the docosahexaenoic acid (DHA, 22:6ω-3), particularly the (4Z,7Z,10Z,13Z,16Z,19Z)-docosa-4,7,10,13,16,19-hexaenoic acid, with the docosahexaenoic acid being especially preferred.

The PUFAs-comprising algal biomass amounts to preferably 2 to 24% by weight, in particular 4 to 22% by weight, preferably 9 to 20% by weight, especially 11 to 18% by weight, of the extrudate, or of the composition employed for preparing the extrudate.

The other foodstuff or feedstuff ingredients are preferably selected from protein-containing, carbohydrate-containing, nucleic-acid-containing and lipid-soluble components and, if appropriate, further fat-containing components and furthermore from among other additives such as minerals, vitamins, pigments and amino acids. Besides, structurants may also be present, besides nutrients, for example so as to improve the texture or the appearance of the feedstuff. Furthermore, it is also possible to employ, for example, binders so as to influence the consistency of the feedstuff. A component which is preferably employed and which constitutes both a nutrient and a structurant is starch.

The extrudate, or the composition employed for preparing the extrudate, preferably has one, preferably all, of the following properties:

a) a total protein content of 33 to 67% by weight, preferably 39 to 61% by weight, particularly 44 to 55% by weight;

b) a total fat content of 5 to 25% by weight, preferably 8 to 22% by weight, in particular 10 to 20% by weight, especially 12 to 18% by weight;

c) a total starch content of not more than 25% by weight, in particular not more than 20% by weight, preferably 6 to 17% by weight, especially preferably 8 to 14% by weight;

d) a polyunsaturated fatty acid (PUFAs) content of 2 to 13% by weight, preferably 3 to 11% by weight, in particular 4 to 10% by weight, especially 5.5 to 9% by weight;

e) an omega-3 fatty acid content of 1 to 7% by weight, preferably 1.5 to 5.5% by weight, in particular 2 to 5% by weight, especially 2.5 to 4.5% by weight;

f) a DHA content of 0.5 to 3% by weight, preferably 0.8 to 2.8% by weight, in particular 1 to 2.8% by weight, especially 1.3 to 2.4% by weight, in particular 1.3 to 2.2% by weight.

Therefore, a composition which is employed in an extrusion process which is preferred in accordance with the invention is a composition which has at least one, preferably all, of the following properties:

a) a total protein content of 33 to 67% by weight, preferably 39 to 61% by weight, particularly 44 to 55% by weight;

b) a total fat content of 5 to 25% by weight, preferably 8 to 22% by weight, in particular 10 to 20% by weight, especially 12 to 18% by weight;

c) a total starch content of not more than 25% by weight, in particular not more than 20% by weight, preferably 6 to 17% by weight, especially preferably 8 to 14% by weight;

d) a polyunsaturated fatty acid (PUFAs) content of 2 to 13% by weight, preferably 3 to 11% by weight, in particular 4 to 10% by weight, especially 5.5 to 9% by weight;

e) an omega-3 fatty acid content of 1 to 7% by weight, preferably 1.5 to 5.5% by weight, in particular 2 to 5% by weight, especially 2.5 to 4.5% by weight;

f) a DHA content of 0.5 to 3% by weight, preferably 0.8 to 2.8% by weight, in particular 1 to 2.8% by weight, especially 1.3 to 2.4% by weight, in particular 1.3 to 2.2% by weight.

A subject matter which is preferred in accordance with the invention is therefore also an extrudate which has at least one, preferably all, of the following properties:
- a) a total protein content of 33 to 67% by weight, preferably 39 to 61% by weight, particularly 44 to 55% by weight;
- b) a total fat content of 5 to 25% by weight, preferably 8 to 22% by weight, in particular 10 to 20% by weight, especially 12 to 18% by weight;
- c) a total starch content of not more than 25% by weight, in particular not more than 20% by weight, preferably 6 to 17% by weight, especially preferably 8 to 14% by weight;
- d) a polyunsaturated fatty acid (PUFAs) content of 2 to 13% by weight, preferably 3 to 11% by weight, in particular 4 to 10% by weight, especially 5.5 to 9% by weight;
- e) an omega-3 fatty acid content of 1 to 7% by weight, preferably 1.5 to 5.5% by weight, in particular 2 to 5% by weight, especially 2.5 to 4.5% by weight;
- f) a DHA content of 0.5 to 3% by weight, preferably 0.8 to 2.8% by weight, in particular 1 to 2.8% by weight, especially 1.3 to 2.4% by weight, in particular 1.3 to 2.2% by weight.

A composition which is employed in an extrusion process which is especially preferred in accordance with the invention is a composition which has the following properties:
- a) a total protein content of 33 to 67% by weight, preferably 39 to 61% by weight, particularly 44 to 55% by weight;
- b) a total fat content of 5 to 25% by weight, preferably 8 to 22% by weight, in particular 10 to 20% by weight, especially 12 to 18% by weight;
- c) a total starch content of not more than 25% by weight, in particular not more than 20% by weight, preferably 6 to 17% by weight, especially preferably 8 to 14% by weight;
- d) a Labyrinthulea biomass content, in particular a Thraustochytriaceae biomass content, of 2 to 24% by weight, preferably 4 to 22% by weight, in particular 9 to 20% by weight, especially 11 to 18% by weight;
- e) a polyunsaturated fatty acid (PUFAs) content of 2 to 13% by weight, preferably 3 to 11% by weight, in particular 4 to 10% by weight, especially 5.5 to 9% by weight;
- f) an omega-3 fatty acid content of 1 to 7% by weight, preferably 1.5 to 5.5% by weight, in particular 2 to 5% by weight, especially 2.5 to 4.5% by weight;
- g) a DHA content of 0.5 to 3% by weight, preferably 0.8 to 2.8% by weight, in particular 1 to 2.8% by weight, especially 1.3 to 2.4% by weight, in particular 1.3 to 2.2% by weight.

Subject matter of the present invention is therefore also an extrudate which comprises the abovementioned components.

A composition which is employed in an extrusion process which is very especially preferred in accordance with the invention is a composition which has the following properties:
- a) a total protein content of 33 to 67% by weight, preferably 39 to 61% by weight, particularly 40 to 50% by weight;
- b) a total fat content of 5 to 25% by weight, preferably 8 to 22% by weight, in particular 10 to 20% by weight, especially 12 to 18% by weight;
- c) a total starch content of not more than 25% by weight, in particular not more than 20% by weight, preferably 6 to 17% by weight, especially preferably 8 to 14% by weight;
- d) an Aurantiochytria biomass content, in particular an *Aurantiochytrium limacinum* biomass content, especially an *Aurantiochytrium limacinum* SR21 biomass content, of 2 to 24% by weight, preferably 4 to 22% by weight, in particular 9 to 20% by weight, especially 11 to 18% by weight;
- e) a polyunsaturated fatty acid (PUFAs) content of 2 to 13% by weight, preferably 3 to 11% by weight, in particular 4 to 10% by weight, especially 5.5 to 9% by weight;
- f) an omega-3 fatty acid content of 1 to 7% by weight, preferably 1.5 to 5.5% by weight, in particular 2 to 5% by weight, especially 2.5 to 4.5% by weight;
- g) a DHA content of 0.5 to 3% by weight, preferably 0.8 to 2.8% by weight, in particular 1 to 2.8% by weight, especially 1.3 to 2.4% by weight, in particular 1.3 to 2.2% by weight.

Accordingly, the extrudate obtained likewise has the abovementioned properties with increasing preference.

In a preferred embodiment, the resulting extrudate is subsequently coated with oil, in particular vegetable oil, preferably in an amount of from 3 to 18% by weight, in particular 5 to 15% by weight, especially preferably 7 to 13% by weight, based on the final product.

Correspondingly, this gives an oil-coated extrudate which preferably has the following properties:
- a) a total protein content of 30 to 60% by weight, preferably 35 to 55% by weight, particularly 40 to 50% by weight;
- b) a total fat content of 15 to 35% by weight, preferably 18 to 32% by weight, in particular 20 to 30% by weight, especially 22 to 28% by weight;
- c) a total starch content of not more than 25% by weight, in particular not more than 20% by weight, preferably 5 to 15% by weight, especially preferably 7 to 13% by weight;
- d) a polyunsaturated fatty acid (PUFAs) content of 2 to 12% by weight, preferably 3 to 10% by weight, in particular 4 to 9% by weight, especially 5 to 8% by weight;
- e) an omega-3 fatty acid content of 1 to 6% by weight, preferably 1.5 to 5% by weight, in particular 2 to 4.5% by weight, especially 2.5 to 4% by weight;
- f) a DHA content of 0.5 to 3% by weight, preferably 0.8 to 2.5% by weight, in particular 1 to 2.5% by weight, especially 1.2 to 2.2% by weight, in particular 1.2 to 2.0% by weight.

The resulting oil-coated extrudate especially preferably has the following properties:
- a) a total protein content of 30 to 60% by weight, preferably 35 to 55% by weight, particularly 40 to 50% by weight;
- b) a total fat content of 15 to 35% by weight, preferably 18 to 32% by weight, in particular 20 to 30% by weight, especially 22 to 28% by weight;
- c) a total starch content of not more than 25% by weight, in particular not more than 20% by weight, preferably 5 to 15% by weight, especially preferably 7 to 13% by weight;
- d) a polyunsaturated fatty acid (PUFAs) content of 2 to 12% by weight, preferably 3 to 10% by weight, in particular 4 to 9% by weight, especially 5 to 8% by weight;

e) an omega-3 fatty acid content of 1 to 6% by weight, preferably 1.5 to 5% by weight, in particular 2 to 4.5% by weight, especially 2.5 to 4% by weight;
f) a DHA content of 0.5 to 3% by weight, preferably 0.8 to 2.5% by weight, in particular 1 to 2.5% by weight, especially 1.2 to 2.2% by weight, in particular 1.2 to 2.0% by weight.

The resulting oil-coated extrudate very especially preferably has the following properties:
a) a total protein content of 30 to 60% by weight, preferably 35 to 55% by weight, particularly 40 to 50% by weight;
b) a total fat content of 15 to 35% by weight, preferably 18 to 32% by weight, in particular 20 to 30% by weight, especially 22 to 28% by weight;
c) a total starch content of not more than 25% by weight, in particular not more than 20% by weight, preferably 5 to 15% by weight, especially preferably 7 to 13% by weight;
d) a Labyrinthulea biomass content, in particular a Thraustochytriaceae biomass content, of 2 to 22% by weight, preferably 4 to 20% by weight, in particular 8 to 18% by weight, especially 10 to 16% by weight;
e) a polyunsaturated fatty acid (PUFAs) content of 2 to 12% by weight, preferably 3 to 10% by weight, in particular 4 to 9% by weight, especially 5 to 8% by weight;
f) an omega-3 fatty acid content of 1 to 6% by weight, preferably 1.5 to 5% by weight, in particular 2 to 4.5% by weight, especially 2.5 to 4% by weight;
g) a DHA content of 0.5 to 3% by weight, preferably 0.8 to 2.5% by weight, in particular 1 to 2.5% by weight, especially 1.2 to 2.2% by weight, in particular 1.2 to 2.0% by weight.

An oil-coated extrudate obtained in accordance with the invention especially has the following properties:
a) a total protein content of 30 to 60% by weight, preferably 35 to 55% by weight, particularly 40 to 50% by weight;
b) a total fat content of 15 to 35% by weight, preferably 18 to 32% by weight, in particular 20 to 30% by weight, especially 22 to 28% by weight;
c) a total starch content of not more than 25% by weight, in particular not more than 20% by weight, preferably 5 to 15% by weight, especially preferably 7 to 13% by weight;
d) an Aurantiochytria biomass content, in particular an *Aurantiochytrium limacinum* biomass content, especially an *Aurantiochytrium limacinum* SR21 biomass content, of 2 to 22% by weight, preferably 4 to 20% by weight, in particular 8 to 18% by weight, especially 10 to 16% by weight;
e) a polyunsaturated fatty acid (PUFAs) content of 2 to 12% by weight, preferably 3 to 10% by weight, in particular 4 to 9% by weight, especially 5 to 8% by weight;
f) an omega-3 fatty acid content of 1 to 6% by weight, preferably 1.5 to 5% by weight, in particular 2 to 4.5% by weight, especially 2.5 to 4% by weight;
g) a DHA content of 0.5 to 3% by weight, preferably 0.8 to 2.5% by weight, in particular 1 to 2.5% by weight, especially 1.2 to 2.2% by weight, in particular 1.2 to 2.0% by weight.

In accordance with the invention, fats, in particular oils, both of animal and of vegetable origin, may be employed as the fat-comprising component besides the biomass to be employed in accordance with the invention. Suitable fat-comprising components are, in accordance with the invention, in particular vegetable oils, for example soya oil, rapeseed oil, sunflower oil, flax seed oil or palm oil, and mixtures of these. If appropriate, fish oil may additionally also be employed in small amounts as fat-comprising component.

Preferably, an oil-coated extrudate according to the invention comprises vegetable oils in an amount of from 3 to 18% by weight, in particular 5 to 15% by weight, especially 7 to 13% by weight. As described above, the vegetable oil is preferably applied to the extrudate at a later point in time, in particular by vacuum coating.

In accordance with the invention, for example soya protein, pea protein, wheat gluten or maize gluten and mixtures of these may be employed as protein-comprising component.

The following examples may be employed as a protein-containing component which additionally contains fats: fish meal, krill meal, bivalve meal, squid meal or shrimp shells. These are hereinbelow summed up by the term "marine meal". In a preferred embodiment, a feedstuff according to the invention comprises marine meal, preferably fish meal, in an amount of from 3 to 18% by weight, in particular 5 to 15% by weight, especially 7 to 13% by weight.

For example wheat meal, sunflower meal or soya meal and mixtures of these may be employed as carbohydrate-comprising component.

An extrudate according to the invention is preferably distinguished not only by the high oil load capacity, but also by having very high abrasion resistance. The abrasion resistance is preferably at least 91%, in particular at least 92 or 93%, especially preferably at least 94%.

The abrasion resistance is determined in the following manner in accordance with the invention: The dried extrudate (4 mm in diameter and 4 mm in length) was exposed to a mechanical load using the Holmen pellet tester NHP100 (Borregaard Lignotech, Hull, UK). Before carrying out the test, the samples were screened so as to remove any adhering fines. The prepared samples (100 g) were subsequently introduced into the pellet tester using a 2.5 mm filter screen. The pellets were subsequently conveyed for 30 seconds at high air speed (approximately 70 mbar) through a small tube with rectangular quadrant pipe. The test parameters are dictated by the equipment. Thereafter, the abraded material was determined by weighing. The abrasion resistance was indicated as PDI (Pellet Durability Index), defined as the percentage amount of sample remaining in the filter screen after carrying out the test. The test was carried out in each case with three samples, and the mean was then calculated.

The oil-loaded extrudate is preferably distinguished by having very high stability in water. This preferably amounts to at least 96%, in particular at least 97%, especially preferably at least 98%.

The stability in water was carried out with the oil-loaded samples. The method was carried out essentially as described by Baeverfjord et al. (2006; Aquaculture 261, 1335-1345), with minor modifications. 10 g samples of the extrudate (in each case 4 mm in length and diameter) were placed into metal infusion baskets (Inox, Germany) of diameter 6.5 mm and mesh size 0.3 mm. The infusion baskets were subsequently placed into a plastic tub filled with water so that the samples were fully covered by water. The tub was subsequently exposed to 30 minutes of shake agitation of 30 shake units per minute, using the multiorbital shaker PSU-20I (Biosan, Latvia). Thereafter, the samples were dried carefully with blotting paper and subsequently weighed before and after they had been subjected to 24 hours of oven drying at a temperature of 105° C. The water stability was calculated as the difference of the sample's dry weight before and after incubation in water and given in percent of the dry weight of the sample employed before incubation with water.

The foodstuff or feedstuff is preferably a product for use in aquaculture or a foodstuff or feedstuff for use in poultry production, pig production or cattle production. The feedstuff may also take the form of a feedstuff which is employed for growing small organisms which may be employed as feedstuff in aquaculture. The small organisms may take the form of, for example, nematodes, crustaceans or rotifers. The feedstuff is preferably present in the form of flakes, spheres or tablets. A feedstuff obtainable by extrusion has a moisture content of preferably less than 5% by weight, especially preferably 0.2 to 4% by weight.

The feedstuff for use in aquaculture is preferably used for breeding finfish and crustaceans which are preferably intended for human nutrition. These include, in particular, carp, tilapia, catfish, tuna, salmon, trout, barramundi, bream, perch, cod, shrimps, lobster, crabs, prawns and crayfish. It is especially preferably a feedstuff for salmon farming. Preferred types of salmon in this context are the Atlantic salmon, red salmon, masu salmon, king salmon, keta salmon, coho salmon, Danube salmon, Pacific salmon and pink salmon.

Alternatively, it may also be a feedstuff intended for farming fish which are subsequently processed to give fish meal or fish oil. These fish are preferably herring, pollack, menhaden, anchovies, caplin or cod. The fish meal or fish oil thus obtained, in turn, can be used in aquaculture for farming edible fish or crustaceans.

Aquaculture may take place in ponds, tanks, basins or else in segregated areas in the sea or in lakes, in particular in this case in cages or net pens. Aquaculture may be used for farming the finished edible fish, but also may be used for farming fry which are subsequently released so as to restock the wild fish stocks.

In salmon farming, the fish are preferably first grown into smolts in freshwater tanks or artificial watercourses and then grown on in cages or net pens which float in the sea and which are preferably anchored in bays or fjords.

Accordingly, further subject matter of the present invention is also a method for farming animals, in particular finfish or crustaceans, preferably salmon, in which a feedstuff according to the invention is employed. Further subject matter of the present invention is additionally an animal, in particular a finfish or shellfish, which is obtainable by such a method according to the invention.

Processes for production of biomass, particularly that biomass which contains cells comprising lipids, particularly PUFAs, particularly from the order Thraustochytriales, are described extensively in the prior art. As a rule, the production takes place by cells being cultured in a fermenter in the presence of a carbon source and of a nitrogen source. In this context, biomass densities of more than 100 grams per litre and production rates of more than 0.5 gram of lipid per litre per hour may be attained. The process is preferably carried out in what is known as a fed-batch process, i.e. the carbon and nitrogen sources are fed in incrementally during the fermentation. When the desired biomass has been obtained, lipid production may be induced by various measures, for example by limiting the nitrogen source, the carbon source or the oxygen content or combinations of these.

Preferably, the cells are fermented in a medium with low salinity, in particular so as to avoid corrosion. This can be achieved by employing chlorine-free sodium salts as the sodium source instead of sodium chloride, such as, for example, sodium sulphate, sodium carbonate, sodium hydrogencarbonate or soda ash. Preferably, chloride is employed in the fermentation in amounts of less than 3 g/l, in particular less than 500 mg/l, especially preferably less than 100 mg/l.

Suitable carbon sources are both alcoholic and non-alcoholic carbon sources. Examples of alcoholic carbon sources are methanol, ethanol and isopropanol. Examples of non-alcoholic carbon sources are fructose, glucose, sucrose, molasses, starch and corn syrup.

Suitable nitrogen sources are both inorganic and organic nitrogen sources. Examples of inorganic nitrogen sources are nitrates and ammonium salts, in particular ammonium sulphate and ammonium hydroxide. Examples of organic nitrogen sources are amino acids, in particular glutamate, and urea.

In addition, inorganic or organic phosphorus compounds and/or known growth-stimulating substances such as, for example, yeast extract or corn steep liquor may also be added so as to have a positive effect on the fermentation.

In an embodiment which is preferred in accordance with the invention, the amount of sulphate added during the fermentation is chosen such that a sulphate content of 25 to 60 g/kg, in particular 25 to 50, 25 to 40 or 25 to 35 g/kg, based on the dry matter, is established in the resulting biomass.

In accordance with the invention, the sulphate content in the resulting biomass can be adjusted in different ways.

In a so-called batch method, for example, the required amount of sulphate may already be introduced in its entirety at the beginning. The amount of sulphate required can be calculated in a simple fashion because the cells employed for forming the biomass virtually completely assimilate the sulphate.

When using a so-called fed-batch method, alternatively, the amount of sulphate required can be metered in over the course of the fermentation or, correspondingly, some of the sulphate may be initially introduced and the remainder may be metered in over the course of the fermentation.

By subsequently metering in sulphate, it can be ensured that the resulting biomass comprises the preferred amount of sulphate, in particular in the case when it emerges over the course of the fermentation that the amount of biomass produced exceeds the originally calculated value.

The sulphate salt employed is preferably sodium sulphate, ammonium sulphate or magnesium sulphate and mixtures of these.

During the fermentation, the chloride content relative to the liquid fermentation medium including the biomass present, is preferably always below 3 g/kg, in particular below 1 g/kg, especially preferably below 400 mg/kg of fermentation medium.

Besides sulphates and chlorides which are optionally employed, it is possible, during the fermentation, optionally also to employ further salts, in particular selected from among sodium carbonate, sodium hydrogencarbonate, soda ash or inorganic phosphorus compounds.

If further salts are employed, they are preferably employed in such an amount that each individual salt during the fermentation is present in each case in an amount of less than 10 g/kg, in particular less than 5 g/kg, especially preferably less than 3 g/kg in the fermentation medium, based on the liquid fermentation medium including the biomass which is present.

The total salt content in the fermentation medium including the biomass which is present, in accordance with the invention, preferably always amounts to below 35 g/kg, in particular to below 30 g/kg, over the course of the entire fermentation. Especially preferably, the total salt content during the entire fermentation amounts to between 10 and 35 kg/g, in particular between 12 and 30 g/kg, based on the liquid fermentation medium including the biomass which is present.

In accordance with the invention, the sulphate content in the fermentation medium including the biomass which is present preferably always amounts to between 5 and 16 g/kg over the course of the entire fermentation.

In accordance with the invention, "sulphate content" is understood as meaning the total sulphate content, that is the content of free and bound, in particular organically bound, sulphate. It can be assumed that the majority of the sulphate which is present in the biomass is present as a component of exopolysaccharides which participate in the formation of the microorganisms' cell wall.

In accordance with the invention, the sulphate content is preferably determined by determining the sulphur content of the biomass obtained since the majority of the sulphur which is present in the biomass can be attributed to the sulphate which is present. Sulphur which can be attributed to other sources can be disregarded owing to the amount of the sulphate which is present. Therefore, the amount of the sulphur determined can be used readily for determining the amount of sulphate which is present.

In this context, the sulphur content of the biomass is preferably determined by elemental analysis as per DIN EN ISO 11885. To analyse the sulphur content of the biomass, suitable aliquots of the sample are hydrolysed before the analysis, preferably using nitric acid and hydrogen peroxide, at 240° C. under pressure so as to ensure that the sulphur which is present is readily available.

In accordance with the invention, therefore, it is preferred for the preparation of the feedstuff to employ a PUFAs-comprising biomass which is distinguished in that a sulphur content of from 8 to 20 g/kg, based on the dry matter, can be detected in said biomass by elemental analysis as per DIN EN ISO 11885. In this context, the sulphur content in the biomass preferably amounts to 8 to 17 g/kg, in particular 8 to 14 g/kg, especially preferably 8 to 12 g/kg, in each case based on the dry matter.

In accordance with the invention, the phosphorus content of biomasses which are preferably employed in accordance with the invention preferably amounts to 1 to 6 g/kg, in particular 2 to 5 g/kg, based on the dry matter. Preferably, the phosphorus content is likewise determined by elemental analysis as per DIN EN ISO 11885.

The cells are preferably fermented at a pH of 3 to 11, in particular 4 to 10, and preferably at a temperature of at least 20° C., in particular 20 to 40° C., especially preferably at least 30° C. A typical fermentation process takes up to approximately 100 hours.

The cells are fermented in accordance with the invention until a biomass density of preferably at least 50, 60 or 70 g/l, in particular of at least 80 or 90 g/l, especially preferably at least 100 g/l, has been reached. The data here refer to the dry biomass content based on the total volume of the fermentation liquor after the fermentation has ended. The dry biomass content is determined by removing the biomass from the fermentation liquor by filtration, followed by washing with water and thereafter complete drying—for example in a microwave oven—and, finally, determining the dry weight.

After the fermentation has ended, the biomass is harvested. After harvesting the biomass or even optionally shortly before harvesting the biomass, the cells are preferably pasteurized in order to kill the cells and to inactivate enzymes which might promote lipid degradation. The pasteurization is preferably effected by heating the biomass to a temperature of 50 to 121° C. for a period of 5 to 60 minutes.

Likewise, after harvesting the biomass or even optionally shortly before harvesting the biomass, antioxidants are preferably added in order to protect the material of value present in the biomass from oxidative degradation. Preferred antioxidants in this context are BHT, BHA, TBHA, ethoxyquin, beta-carotene, vitamin E and vitamin C. The antioxidant, if used, is preferably added in an amount of 0.01 to 2% by weight.

Before the actual drying, a portion of the fermentation medium may now optionally already be separated from the biomass and the solid fraction can thus be increased. This may be carried out in particular by centrifugation, flotation, filtration, particularly ultrafiltration or microfiltration, decanting and/or solvent evaporation. In this case the solvent is preferably evaporated using a rotary evaporator, a thin-film evaporator or a falling-film evaporator in a single-stage or multistage process. Alternatively, reverse osmosis, for example, is also useful for concentrating the fermentation broth.

In this first optional but preferred step, the fermentation broth is preferably concentrated to a solids content of at least 10 or 15% by weight, preferably of at least 20 or 25% by weight, particularly 10 to 50 or 15 to 45% by weight, particularly preferably 15 to 40% by weight or 20 to 40% by weight.

This means that the biomass to be dried in a method according to the invention is preferably present in the form of a suspension having the solid fraction stated above, where the suspension is preferably a fermentation broth or concentrated fermentation broth.

After the optional concentration of the fermentation broth, the biomass is then dried in accordance with the invention, preferably by spray drying, particularly nozzle spray drying, spray granulation, fluidized bed granulation, particularly fluidized bed granulation, or in a drum dryer.

Alternatively, the biomass may also be subjected to the drying step directly after harvesting without prior concentration, particularly if the fermentation broth obtained already has a high solids content, preferably as stated above.

On drying the biomass, this is preferably dried to a residual moisture content of at most 10% by weight, particularly 0 to 10% by weight, particularly preferably at most 8% by weight, particularly 0.5 to 8% by weight, above all at most 6 or 5% by weight, particularly 0.5 to 6 or 0.5 to 5% by weight.

In accordance with the invention, "dry matter" is, accordingly, preferably to be understood as meaning a product which has a moisture content of below 10% by weight, in particular of below 5% by weight.

A free-flowing, fine-grained or coarse-grained product, preferably a granulate, is preferably obtained by the drying process. A product having the desired particle size can optionally be obtained from the granulate obtained by sieving or dust separation.

Providing a free-flowing fine-grained powder was obtained, this can optionally be converted into a coarse-grained, free-flowing and largely dust-free product, which can be stored, by suitable compacting or granulating processes.

Conventional organic or inorganic auxiliaries or supports such as starch, gelatine, cellulose derivatives or similar substances, which are typically used in food processing or feed processing as binding agents, gelling agents or thickeners, may optionally be used in this subsequent granulation or compacting process.

"Free-flowing" according to the invention is understood to mean a powder that can flow out unhindered from a series of glass efflux vessels having different-size outflow openings, at least from the vessel having the 5 millimetre opening (Klein: Seifen, Öle, Fette, Wachse 94, 12 (1968)).

"Fine-grained" according to the invention is understood to mean a powder having a predominant fraction (>50%) of particle sizes of 20 to 100 micrometres in diameter.

"Coarse-grained" according to the invention is understood to mean a powder having a predominant fraction (>50%) of particle sizes of 100 to 2500 micrometres in diameter.

"Dust-free" according to the invention is understood to mean a powder that contains only low fractions (<10%, preferably <5%) of particle sizes below 100 micrometres.

Grain or particle sizes are preferably determined according to the invention by laser diffraction spectrometric methods. Possible methods are described in the textbook "Teilchengrößenmessung in der Laborpraxis" [Particle size measurement in the laboratory] by R. H. Müller and R. Schuhmann, Wissenschaftliche Verlagsgesellschaft Stuttgart (1996) and in the textbook "Introduction to Particle Technology" by M. Rhodes, Wiley & Sons (1998). Inasmuch as various methods can be used, the first-cited usable method from the textbook of R. H. Müller and R. Schuhmann for the measuring of particle size is preferably used.

The biomass obtained by drying preferably has a fraction of at least 80% by weight, particularly at least 90% by weight, particularly preferably at least 95% by weight, of particles having a particle size of 100 to 3500 micrometres, preferably 100 to 3000 micrometres, above all 100 to 2500 micrometres.

WORKING EXAMPLES

Example 1: Production of the Biomass by Fermentation of *Aurantiochytrium limacinum* SR21 in a Medium with a High Sulphate Content, and Subsequent Drying of the Biomass The cells were cultured for approximately 75 h in a fed-batch process using a steel fermenter with a fermenter volume of 2 litres at a total initial biomass of 712 g and an obtained total final biomass of 1.3-1.5 kg. During the process, a glucose solution (570 g/kg glucose) was metered in ("fed-batch process").

The composition of the starting medium was as follows:

Medium 1: 20 g/kg glucose; 4 g/kg yeast extract; 16 g/kg sodium sulphate; 2 g/kg ammonium sulphate; 2.46 g/kg magnesium sulphate (heptahydrate); 0.45 g/kg potassium chloride; 4.5 g/kg potassium dihydrogenphosphate; 0.1 g/kg thiamine (HCl); 5 g/kg trace element solution.

The composition of the trace element solution was as follows: 35 g/kg aqueous hydrochloric acid (37%); 1.86 g/kg manganese chloride (tetrahydrate); 1.82 g/kg zinc sulphate (heptahydrate); 0.818 g/kg sodium EDTA; 0.29 g/kg boric acid; 0.24 g/kg sodium molybdate (dihydrate); 4.58 g/kg calcium chloride (dihydrate); 17.33 g/kg iron sulphate (heptahydrate); 0.15 g/kg copper chloride (dihydrate).

The cultivation was carried out under the following conditions: Cultivation temperature 28° C.; aeration rate 0.5 vvm, stirrer speed 600-1950 rpm, pH control during the growth phase at 4.5 using ammonia water (25% v/v). The fermentation was carried out until a biomass density of 116 g/l had been reached.

After the cultivation, the fermentation liquors were heated to 60° C. for 20 minutes so as to prevent a further activity of the cells.

This was followed by a two-step drying of the biomass: First, the fermentation liquor was concentrated by evaporation to a dry matter of approximately 20% by weight. Thereafter, the concentrated fermentation liquor was spray-dried using a Production Minor™ Spray Dryer (GEA NIRO) at an inlet temperature of the drying air of 340° C. Spray-drying thus gave a powder with more than 95% by weight of dry matter.

To determine the sulphate content of the biomass obtained, the sulphur content of the biomass was determined as per DIN ISO 11885. To this end, an aliquot of the biomass was first hydrolysed with nitric acid and hydrogen peroxide at 240° C. under pressure. The sulphur content determined amounted to 11 g/kg biomass, which corresponds to a sulphate content of 33 g/kg biomass.

Example 2: Feedstuff Preparation by Extrusion

The feedstuff mixtures particularized in Table 1 were prepared. Besides the biomass of Example 1 to be employed in accordance with the invention, two further commercially available Labyrinthulea biomasses and fish oil as are currently still usual source of omega-3 fatty acids were tested for comparison purposes.

In each case, the feedstuff mixtures were prepared by mixing the components—with the exception of the oils—using a twin-screw mixer (Model 500L, TGC Extrusion, France). The mixtures thus obtained were subsequently comminuted to particle sizes of below 250 μm using a hammer mill (Model SH1, Hosokawa-Alpine, Germany).

TABLE 1

Feedstuff compositions employed in the extrusion process
(Data in % by weight)

| Constituent | M1 | M2 | M3 | M4 |
|---|---|---|---|---|
| Fish meal | 10.00 | 10.00 | 10.00 | 10.00 |
| Soya protein concentrate | 23.10 | 23.20 | 23.10 | 20.27 |
| Pea protein concentrate | 15.00 | 15.00 | 15.00 | 15.00 |
| Wheat gluten | 9.90 | 9.90 | 9.90 | 9.90 |
| Wheat flour | 18.12 | 10.82 | 10.55 | 16.46 |
| Fish oil | 10.00 | — | — | — |
| Biomass from Example 1 | — | 16.00 | — | — |
| Commercially available biomass 1 | — | — | 16.74 | — |
| Commercially available biomass 2 | — | — | — | 13.52 |
| Rape oil | 10.00 | 11.00 | 11.00 | 11.00 |
| Vitamin/mineral premix | 1.00 | 1.00 | 1.00 | 1.00 |
| Dicalcium phosphate | 2.00 | 2.00 | 2.00 | 2.00 |
| Yttrium oxide | 0.03 | 0.03 | 0.03 | 0.03 |
| DL-methionine | 0.35 | 0.36 | 0.33 | 0.33 |
| Aquavi-Lys | 0.17 | 0.35 | 0.08 | 0.19 |
| Tryp-Amino | 0.09 | 0.09 | 0.08 | 0.09 |
| L-Histidine | 0.24 | 0.25 | 0.19 | 0.21 |

For the extrusion, in each case 140 kg were employed per feedstuff. Extruding was carried out by means of a twin-screw extruder (CLEXTRAL BC45) with a screw diameter of 55.5 mm and a maximum flow rate of 90-100 kg/h. Pellets 4.0 mm in size were extruded. To this end, the extruder was equipped with a high-speed cutter so as to convert the product into the desired pellet size.

Various extrusion parameters were then tested so as to find out the extrusion conditions under which an optimal oil load capacity of the extrudate obtained may be obtained. Surprisingly, it has been found that an optimal oil load capacity can be achieved with a very low energy input. The energy input here was markedly lower than when using fish oil. Furthermore, the optimal energy input in a biomass with a high sulphate content preferably to be used in accordance with the invention was, again, markedly lower than in the case of commercially available Thraustochytriales biomasses. The results are shown in Table 2.

TABLE 2

Energy inputs for the preparation of pellets with the desired oil load capacity

| Diet | Barrel 1 Temp (° C.) | Barrel 2 Temp (° C.) | Feeder rate (kg/h) | Rotational speed (rpm) | Amount of water (0-10) | Amperage (A) | SME (Wh/kg) |
|---|---|---|---|---|---|---|---|
| M1 | 31 | 116-118 | 112 | 215 | 9 | 11 | 34.6 |
| M2 | 32 | 98-104 | 141 | 253 | 5 | 7 | 20.6 |
| M3 | 32 | 97-102 | 136 | 255 | 5 | 8 | 24.6 |
| M4 | 31 | 99-107 | 133 | 253 | 5 | 8 | 24.9 |

The parameter "SME" is the specific mechanical energy. It is calculated as follows:

$$SME \text{ (Wh/kg)} = \frac{U \times I \times \cos\Phi \frac{\text{Test } SS}{\text{Max } SS}}{Q_S}$$

where

U: Working voltage of the motor (presently 460 V)
I: Amperage of the motor (A)
cos φ: Theoretical output of the extruder motor (presently 0.95)
Test SS: Test speed (rpm) of the rotating screws
Max SS: Maximum speed (267 rpm) of the rotating screws
$Q_S$: Inlet flow rate of the feed mash (kg/h)

After the extrusion, the extrudate was dried in a vibrating fluidized-bed dryer (Model DR100, TGC Extrusion, France).

Thereafter, the extrudate was cooled and then coated with oil by means of vacuum coating (vacuum coater PG-10VCLAB, Dinnisen, The Netherlands). Here, it was found that more than 0.35 g of oil can be applied to 1 g of extrudate.

Example 3: Determination of the Abrasion Resistance and Water Stability

The abrasion resistance was determined as follows: Before being loaded with oil, the dried extrusion product was exposed to a mechanical stress using the Holmen pellet tester (Borregaard Lignotech, Hull, UK). Before the test was carried out, the samples were sieved so as to remove any adhering fines. The prepared samples (100 g) were subsequently introduced into the pellet tester using a 2.5 mm filter screen. The pellets were subsequently conveyed for 30 seconds at high air speed through a small tube with rectangular quadrant pipe. Thereafter, the abraded material was determined by weighing. The abrasion resistance was indicated as PDI (Pellet Durability Index), defined as the percentage amount of sample remaining on the filter screen. The test was carried out in each case with three samples, and the mean was then calculated.

The stability in water was carried out with the oil-loaded samples. The method was carried out essentially as described by Baeverfjord et al. (2006; Aquaculture 261, 1335-1345), with minor modifications. 10 g samples were placed into metal infusion baskets of mesh size 0.3 mm. The infusion baskets were subsequently placed into a plastic tub filled with water so that the samples were fully covered by water. The tub was subsequently exposed to 30 minutes of shake agitation of 30 shake units per minute. Thereafter, the samples were dried carefully with blotting paper and subsequently weighed before and after they had been subjected to 24 hours of oven drying at a temperature of 105° C. The water stability was calculated as the difference of the sample's dry weight before and after incubation in water and given in percent of the dry weight of the sample employed before incubation with water.

The results are shown in Table 3.

| | Sample | | | |
|---|---|---|---|---|
| | M1 | M2 | M3 | M4 |
| Abrasion resistance [%] | 90.0 | 93.3 | 88.3 | 85.2 |
| Water stability [%] | 95.7 | 98.5 | 93.8 | 90.2 |

It can be seen that a feedstuff according to the invention has a markedly higher abrasion resistance and water stability than feedstuffs which comprise a commercially available Labyrinthulea biomass or fish oil as the source of omega-3 fatty acids.

The invention claimed is:

1. A feedstuff extrudate comprising a PUFA-comprising biomass, wherein the PUFA-comprising biomass comprises microbial cells of the taxon Labyrinthulomycetes, and has a sulphate content of 25 to 60 g/kg based on dry matter, and wherein the feedstuff extrudate has an oil load capacity of at least 0.35 g of oil per g of feedstuff extrudate.

2. The feedstuff extrudate of claim 1, wherein said biomass comprises a sulphate content 25 to 50 g/kg based on the dry matter.

3. The feedstuff extrudate of claim 1, wherein the PUFA-comprising biomass comprises microbial cells of the family Thraustochytriaceae.

4. The feedstuff extrudate of claim 1, wherein the PUFA-comprising biomass comprises microbial cells of the genera: *Thraustochytrium, Schizochytrium, Aurantiochytrium, Oblongichytrium* or *Ulkenia*.

5. The feedstuff extrudate of claim 1, wherein the PUFA-comprising biomass comprises microbial cells of the species *Aurantiochytrium limacinum*.

6. The feedstuff extrudate of claim 1, wherein the biomass has a sulphate content of 25-35 g/kg based on the dry matter.

7. The feedstuff extrudate of claim 1, comprising:
   a) a total protein content of 30 to 60% by weight;
   b) a total fat content of 15 to 35% by weight;
   c) a total starch content of not more than 25% by weight; and
   d) a biomass content of 2 to 22% by weight.

8. The feedstuff extrudate of claim 7, further comprising one or more of:
   e) a polyunsaturated fatty acid (PUFAs) content of 2 to 12% by weight;
   f) an omega-3 fatty acid content of 1 to 6% by weight; and
   g) a DHA content of 0.5 to 3% by weight.

9. The feedstuff extrudate of claim 1, comprising:
a) a total protein content of 40 to 50% by weight;
b) a total fat content of 22 to 28% by weight;
c) a total starch content of 7 to 13% by weight;
d) a Thraustochytriaceae biomass content of 10 to 16% by weight;

and further comprising one or more of the following:
e) a polyunsaturated fatty acid (PUFA) content of 5 to 8% by weight;
f) an omega-3 fatty acid content of 2.5 to 4% by weight; and
g) a DHA content of 1.2 to 2.0% by weight.

10. The feedstuff extrudate of claim 4, wherein the PUFA-comprising biomass has a sulphate content of 25 to 40 g/kg based on the dry matter.

11. The feedstuff extrudate of claim 10, further comprising:
a) a total protein content of 35 to 55% by weight;
b) a total fat content 18 to 32% by weight; and
c) a total starch content of 5 to 15% by weight.

12. The feedstuff extrudate of claim 11, further comprising:
d) a Thraustochytriaceae biomass content of 4 to 20% by weight;
e) a polyunsaturated fatty acid (PUFAs) content of 3 to 10% by weight;
f) an omega-3 fatty acid content of 2 to 4.5% by weight; and
g) a DHA content of 0.8 to 2.5% by weight.

13. A method of growing animals by feeding them a feedstuff extrudate comprising a PUFA-comprising biomass, wherein the PUFA-comprising biomass comprises microbial cells of the taxon Labyrinthulomycetes and has a sulphate content of 25 to 60 g/kg based on dry matter, and wherein the feedstuff extrudate has an oil load capacity of at least 0.35 g of oil per g of feedstuff extrudate.

14. The method of growing animals of claim 13, wherein the PUFA-comprising biomass comprises microbial cells of the family Thraustochytriaceae and has a sulphate content of 25 to 50 g/kg, based on the dry matter and wherein the feedstuff extrudate comprises:
a) a total protein content of 30 to 60% by weight;
b) a total fat content of 15 to 35% by weight;
c) a total starch content of not more than 25% by weight; and
d) a biomass content of 2 to 22% by weight.

15. The method of growing animals of claim 13, wherein the biomass comprises microbial cells of the species *Aurantiochytrium limacinum* and wherein the feedstuff extrudate further comprises one or more of the following:
e) a polyunsaturated fatty acid (PUFAs) content of 2 to 12% by weight;
f) an omega-3 fatty acid content of 1 to 6% by weight; and
g) a DHA content of 0.5 to 3% by weight.

16. The method of claim 14, wherein the PUFA-comprising biomass has a sulphate content of 25 to 40 g/kg based on the dry matter.

17. The method of claim 16, wherein the feedstuff extrudate further comprises:
a) a total protein content of 35 to 55% by weight;
b) a total fat content 18 to 32% by weight; and
c) a total starch content of 5 to 15% by weight.

18. The method of claim 17, wherein the feedstuff extrudate further comprises:
d) a Thraustochytriaceae biomass content, of 4 to 20% by weight;
e) a polyunsaturated fatty acid (PUFAs) content of 3 to 10% by weight;
f) an omega-3 fatty acid content of 2 to 4.5% by weight; and
g) a DHA content of 0.8 to 2.5% by weight.

* * * * *